United States Patent [19]
Mick

[11] Patent Number: 5,644,613
[45] Date of Patent: Jul. 1, 1997

[54] ROAD-MAPPING

[75] Inventor: Arnon Mick, Haifa, Israel

[73] Assignee: CMT-Medical Technologies Ltd., Haifa, Israel

[21] Appl. No.: 695,053

[22] Filed: Aug. 9, 1996

[30] Foreign Application Priority Data

Aug. 11, 1995 [IL] Israel .......................................... 114916
Dec. 18, 1995 [IL] Israel .......................................... 116434

[51] Int. Cl.$^6$ .................................................. H05G 1/64
[52] U.S. Cl. ...................................... 378/98.12; 378/98.11
[58] Field of Search ............................. 378/98.11, 98.12, 378/62, 90, 98, 98.2, 98.3, 98.5

[56] References Cited

U.S. PATENT DOCUMENTS 4,555,728  11/1985  Fenster et al. .
5,161,178  11/1992  Honda et al. ................... 378/98.11

*Primary Examiner*—Don Wong
*Attorney, Agent, or Firm*—Kenyon & Kenyon

[57] ABSTRACT

A method of producing a road-mapped image of a body portion for monitored guidance of a catheter therethrough, the method including providing a first X-ray transmission frame of the body portion, injecting contrast-enhancing material into a blood vessel in the body portion, irradiating the body portion with X-ray radiation for a first irradiation session, producing a series of second X-ray transmission frames of the body portion during the first irradiation session, forming a series of third, subtracted, frames each third frame corresponding to the difference between a respective second frame and the first frame, selecting one of the third frames, irradiating the body portion with X-ray radiation for a second irradiation session, guiding the catheter through a blood vessel in the body portion during the irradiation session, producing a first, dynamic, X-ray transmission image including a plurality of fourth frames of the body portion during the second irradiation session and forming a second, dynamic, image of the body portion including a series of fifth, subtracted, frames each fifth frame corresponding to the difference between a respective fourth frame and the second frame corresponding to the selected one of the third frames.

16 Claims, 1 Drawing Sheet

ROAD-MAPPING

FIELD OF THE INVENTION

The present invention relates generally to medical imaging apparatus and, more particularly, to an improved method and apparatus for constructing a "road map" for monitored surgery.

BACKGROUND OF THE INVENTION

Medical imaging apparatus such as digital fluorography systems are well known in the art. For imaging moving objects, such systems operate in a dynamic mode of operation in which a video readout is used. To avoid flicker in the image, the video readout consists of 25–30 frames per second. The X-ray exposure in dynamic imaging systems may be continuous or pulsed, as described in U.S. Pat. No. 4,555,728.

Angiography is a commonly used procedure. Typically, a catheter is guided, through blood vessels, from an insertion site to a target site where a given task is to be carried out. The given task may include, for example, local injection of contrast-enhancing material or expansion of a particular artery using a "balloon" catheter. The position of the surgical instrument during surgery is typically monitored based on dynamic, real time, images of relevant body portions, i.e. body portion en route between the insertion site and the target site. To ensure quick, efficient and accurate guidance of the catheter to the target site, each dynamic image is preferably shown superimposed with a "road-map" image of the corresponding relevant body portion. The road map image outlines the structure, e.g. the blood vessel configuration, of the relevant body portion.

In a prior art system, the road map is constructed based on a static x-ray transmission image of the relevant body portion, produced after injecting contrast-enhancing material into blood vessels of the relevant body portion. The contrast-enhanced blood vessels typically appear as generally darker regions of the static base image. A dynamic, road mapped, image is then formed by subtraction of the blood-vessel-emphasized image from, the dynamic image of the relevant body portion. Since the two images differ substantially only in the blood-vessel-enhanced regions, the subtracted image includes essentially only an outline of the blood-vessel configuration in the relevant body portion superimposed with a dynamic image of the surgical instrument. It is appreciated that the quality of the road mapped image is highly dependent on the quality of the static blood-vessel image from which it is formed and on the correlation between the blood-vessel image and the dynamic image of the treated body portion.

According to one existing method, the blood-vessel-emphasized image is constructed from a series of frames, e.g. a series of frames of a dynamic image, which are produced following an injection of contrast-enhancing material. Since the injected contrast-enhancing material travels with the bloodstream, different frames generally emphasize different blood vessel regions. The different frames may be unfiltered frames or frames which are filtered, for example, using recursive filtering, whereby each frame depends to a predetermined extent on the content of preceding frames.

To obtain a complete image of all the emphasized blood-vessels the series of frames may be combined in accordance with a maximum opacity criterion, whereby each pixel in the combined image is taken from the blood-vessel-emphasized-frame having the highest opacity at that pixel. It has been found that although the maximum opacity criterion enables substantially full coverage of any body region, this technique results in loss of detail, particularly in finer blood-vessels regions. This may be due to slight shifts in the pixel-position of the vessels, between frames, and/or due to inability of discriminating, electronically, between the finer blood vessels and arbitrary noise in the image.

SUMMARY OF THE INVENTION

It is an object of the present invention to provide an improved method of producing a road-mapped image for monitoring the position of a catheter in a given body portion. It is a further object of the present invention to provide a system for monitoring the position of the catheter in the body portion.

There is thus provided, in accordance with a preferred embodiment of the invention, a method of producing a road-mapped image of a body portion for monitored guidance of a catheter therethrough, the method including:

providing a first X-ray transmission frame of the body portion;

injecting contrast-enhancing material into a blood vessel in the body portion;

irradiating said body portion with X-ray radiation for a first irradiation session;

producing a series of second X-ray transmission frames of the body portion during the first irradiation session;

forming a series of third, subtracted, frames each third frame corresponding to the difference between a respective second frame and the first frame;

selecting one of the third frames;

irradiating the body portion with X-ray radiation for a second irradiation session;

guiding the catheter through a blood vessel in the body portion during the second irradiation session;

producing a first, dynamic, X-ray transmission image including a plurality of fourth frames of the body portion during the second irradiation sequence; and forming a second, dynamic, image of the body portion including a plurality of fifth, subtracted, frames each fifth frame corresponding to the difference between a respective fourth frame and the second frame corresponding to the selected one of the third frames.

In a preferred embodiment of the present invention, forming a series of third frames includes subtracting the first frame from each of the second frames.

Further, in a preferred embodiment of the invention, forming a second dynamic image includes subtracting each of the fourth frames from the second frame corresponding to the selected one of the third frames.

In one preferred of the present invention, selecting one of the third frames includes sequentially displaying the third frames and terminating the X-ray radiation at a desired third frame. Alternatively, in a preferred embodiment, selecting one of the third frames includes displaying a plurality of the third frames simultaneously and selecting one of the displayed third frames.

BRIEF DESCRIPTION OF THE DRAWINGS

The present invention will be better understood and appreciated from the following detailed description, taken in conjunction with the following drawings in which.

DETAILED DESCRIPTION OF PREFERRED EMBODIMENTS

Figure 1:
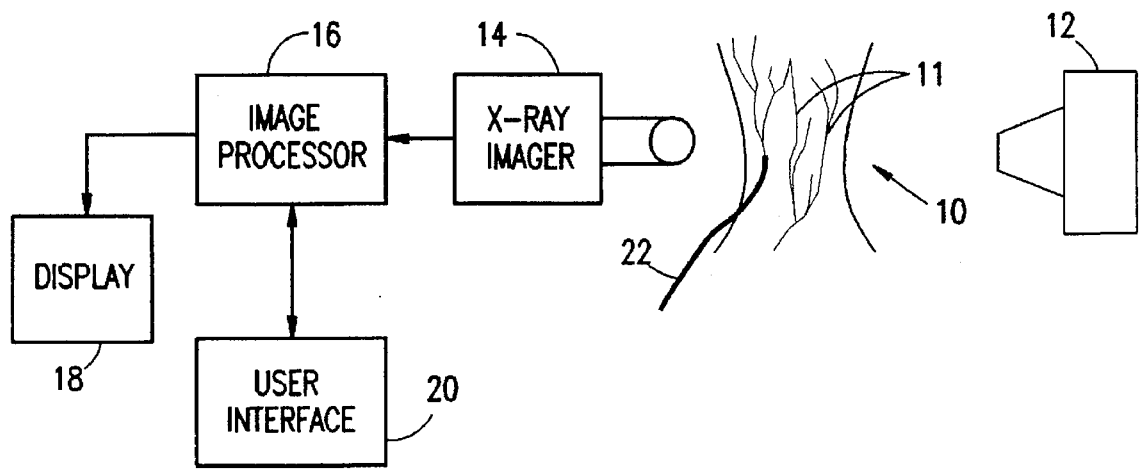
FIG. 1 is a schematic, block diagram, illustration of a system for producing a road mapped image, constructed and operative in accordance with a preferred embodiment of the present invention.

Reference is now made to FIG. 1 which schematically illustrates a system for producing a road mapped image in accordance with a preferred embodiment of the present invention. The system of FIG. 1 includes an X ray emitter 12 positioned for irradiating a body portion 10 which comprises a plurality of blood vessels 11 as known in the art. An X ray transmission video imager 14, as is known in the art, produces a video image including a plurality of frames of portion 10, typically at a rate of 25–30 frames per second. The video image from imager 14 is processed by an image processor 16 and displayed on a video display 18 associated with processor 16. Image processor 16 is also associated with a user interface 20 which enables a user to control the image displayed on display 18, as described in detail below. The system of FIG. 1 is adapted for monitoring surgical activity in body portion 10, such as guiding a catheter 22 through certain vessels 11 in portion 10.

To reduce noise in the displayed images, image processor 16 preferably employs circuitry or software for recursive filtering of the frames produced by imager 14, whereby each frame of the displayed image is dependent to a predetermined extent on previous images, as is known in the art. In a preferred embodiment of the invention, the intensity, $I_o$, of each pixel in a given, displayed, frame is calculated based on the following equation:

$$I_o = \alpha I_n + (1-\alpha)\alpha I_{n-1} + (1-\alpha)^2 \alpha I_{n-2} + \ldots + (1-\alpha)^j \alpha I_{n-j} + \ldots + (1-\alpha)^{n-1} \alpha I_1 \quad (1)$$

wherein $I_n$ is the intensity of the last input frame, $I_j$ [j=1 .. (n-1)] are the intensities of the pixel in previous images and $\alpha$ is a predetermined constant. Although recursive filtering yielding output pixel intensities as in equation (1) is preferred, other filtering methods may also be suitable or unfiltered images be used.

As in prior art systems, the dynamic image of portion 10 viewed on display 18 is a road-mapped image including a generally dark representation of catheter 22 on a road-map background which consists of a generally bright representation of the configuration of blood vessels 11 in portion 10. However, the road-mapped image of the present invention is constructed according to a new method, described below, which provides improved resolution in mapping the blood vessel configuration in body portion 10. The road-mapped image of the present invention is produced by processor 16 based on an image selected by the user using interface 20.

Figure 2:
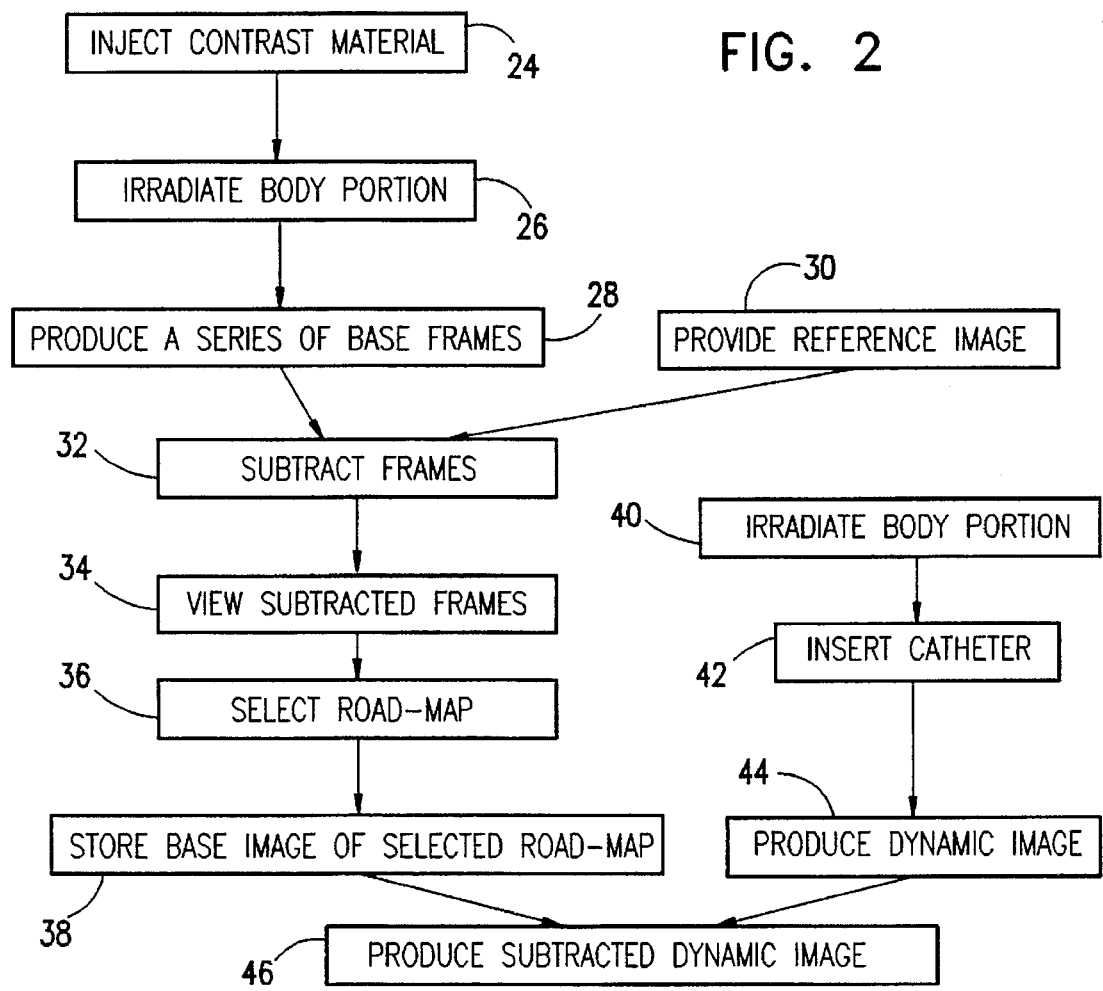
FIG. 2 is a schematic flow chart illustrating a method of producing a road mapped image using a system as in FIG. 1.

Reference is now made also to FIG. 2 which is a schematic flow chart illustrating a method of producing a road-mapped image of region 10 using the system shown in FIG. 1. According to the present method, as indicated at block 24, contrast-enhancing material is injected into a selected region of body portion 10. As known in the art, the contrast-enhancing material travels with the blood stream spreading through blood-vessels 11 into other regions of portion 10. As the contrast-enhancing material travels, body portion 10 is irradiated with X ray radiation for a preliminary irradiation session, as indicated at block 26, and imager 14 produces a series of X-ray transmission base frames of body portion 10, as indicated at block 28. The series of X-ray transmission base frames thus produced are preferably filtered to reduce noise, for example using recursive filtering as described above. Since the different X-ray transmission frames are separated in time, different blood vessel regions of portion 10 are emphasized by different frames.

In a preferred embodiment of the invention, prior to the injection of contrast-enhancing material, a static reference image of body portion 10 with no contrast-enhancing material is produced by imager 14 and stored in a memory of processor 16, as indicated at block 30. A subtracter in processor 16 subtracts the static reference image from each of the series of X-ray transmission frames, thereby constructing a series of blood-vessel emphasized, subtracted, frames of body portion 10, as indicated at block 32. The subtracted frames show contrast-material-bearing blood vessels 11 as generally dark "roads" on a generally brighter gray background. Thus, each subtracted frame defines a "negative" road-map image emphasizing different blood vessel regions in body portion 10, in accordance with the spread of contrast-enhancing material. In an alternative embodiment, the series of contrast enhanced X-ray transmission frames are subtracted from the static reference image, resulting in a "positive" road-map image, showing contrast-material-bearing blood vessels 11 as generally bright "roads" on a generally darker, gray, background. The series of subtracted frames produced by either of the methods described above is then displayed, either sequentially or simultaneously, on display 18 to enable the user to view the subtracted frames and to compare them, as indicated at block 34.

In a preferred embodiment of the present invention, as indicated at block 36, the user selects one of the subtracted frames, preferably a frame which best emphasizes the blood-vessel configuration in a region of body portion 10 where monitored guidance of the catheter is required. Once the desired subtracted frame has been selected, the selection is entered to processor 16 using user interface 20. Processor 16 then stores in the memory thereof the unsubtracted, blood-vessel emphasized, frame corresponding to the subtracted frame selected by the user, as indicated at block 38. The stored, unsubtracted, frame is subsequently used as a base image for producing a dynamic, road-mapped, image of portion 10 during guidance of catheter 22 therethrough, as described below.

In one preferred of the present invention, the subtracted frames are displayed to the user sequentially, in the form of a dynamic image, and the user selects a desired frame by terminating the X-ray radiation upon display of the desired frame. In an alternative, preferred, embodiment of the present invention, a number of the subtracted frames are displayed simultaneously and the user selects one of the displayed frames.

After the desired base frame has been selected and stored, as described above, body portion 10 is irradiated with continuous or pulsed X ray radiation, as indicated at block 40, in accordance with a predetermined irradiation sequence as is known in the art. Catheter 22 is then inserted into body portion 10, as indicated at block 42, and is guided through blood-vessels 11 to the desired target site. Imager 14 produces a dynamic, X-ray transmission, video image of body portion 10, as indicated at block 44. The dynamic video image is received by processor 16 which produces a road-mapped image of body portion 10 by subtracting the dynamic video image from the base image stored in the memory of the processor, as indicated at block 46. The subtracted, road mapped, image thus produced shows catheter 22 as a generally dark object being guided through blood vessels 11 which are generally bright. It should be noted that the road map image thus produced may clearly map only a relatively small region of body portion 10, however, the blood-vessel resolution in the mapped region is very high compared to that of existing road-mapped images.

Once catheter 22 reaches the desired target site, a given task may be performed at that target site, for example local injection of contrast-enhancing material or expansion of a given blood vessel, as known in the art.

The present invention has been described above in a context of a dedicated hardware system. However, it should be appreciated that at least some aspects of the present invention may be executed by computer software, as is well known in the art.

It will be appreciated by persons skilled in the art that the present invention is not limited by what has been particularly shown and described hereinabove. Rather, the scope of the present invention is defined only by the claims which follow:

I claim:

1. A method of producing a road-mapped image of a body portion for monitored guidance of a catheter therethrough, the method comprising the steps of:

provinding a first X-ray transmission frame of said body portion;

injecting contrast-enhancing material into a blood vessel in said body portion;

irradiating said body portion with X-ray radiation for a first irradiation session;

producing a series of second X-ray transmission frames of the body portion during said first irradiation session;

forming a series of third, subtracted, frames each third frame corresponding to the difference between a respective second frame and said first frame;

selecting one of said third frames;

irradiating said body portion with X-ray radiation for a second irradiation session;

guiding said catheter through a blood vessel in said body portion during said second irradiation session;

producing a first, dynamic, X-ray transmission image including a plurality of fourth frames of said body portion during said second irradiation session; and forming a second, dynamic, image of said body portion including a series of fifth, subtracted, frames, each fifth frame corresponding to the difference between a respective fourth frame and the second frame corresponding to the selected one of said third frames.

2. A method according to claim 1 wherein forming the series of third frames comprises subtracting said first frame from each of said second frames.

3. A method according to claim 1 wherein forming the second dynamic image comprises subtracting each of said fourth frames from the second frame corresponding to the selected one of said third frames.

4. A method according to claim 2 wherein forming the second dynamic image comprises subtracting each of said fourth frames from the second frame corresponding to the selected one of said third frames.

5. A method according to claim 1 wherein selecting one of said third frames comprises sequentially displaying said third frames and terminating the X-ray radiation at a selected third frame.

6. A method according to claim 2 wherein selecting one of said third frames comprises sequentially displaying said third frames and terminating the X-ray radiation at a selected third frame.

7. A method according to claim 3 wherein selecting one of said third frames comprises sequentially displaying said third frames and terminating the X-ray radiation at a selected third frame.

8. A method according to claim 4 wherein selecting one of said third frames comprises sequentially displaying said third frames and terminating the X-ray radiation at a selected third frame.

9. A method according to claim 1 wherein selecting one of said third frames comprises displaying a plurality of said third frames simultaneously and selecting one of the displayed third frames.

10. A method according to claim 2 wherein selecting one of said third frames comprises displaying a plurality of said third frames simultaneously and selecting one of the displayed third frames.

11. A method according to claim 3 wherein selecting one of said third frames comprises displaying a plurality of said third frames simultaneously and selecting one of the displayed third frames.

12. A method according to claim 4 wherein selecting one of said third frames comprises displaying a plurality of said third frames simultaneously and selecting one of the displayed third frames.

13. A method according to claim 5 wherein selecting one of said third frames comprises displaying a plurality of said third frames simultaneously and selecting one of the displayed third frames.

14. A method according to claim 6 wherein selecting one of said third frames comprises displaying a plurality of said third frames simultaneously and selecting one of the displayed third frames.

15. A method according to claim 7 wherein selecting one of said third frames comprises displaying a plurality of said third frames simultaneously and selecting one of the displayed third frames.

16. A method according to claim 8 wherein selecting one of said third frames comprises displaying a plurality of said third frames simultaneously and selecting one of the displayed third frames.

* * * * *